US009921243B2

United States Patent
Digmann et al.

(10) Patent No.: US 9,921,243 B2
(45) Date of Patent: Mar. 20, 2018

(54) SYSTEM AND METHOD FOR VOLTAGE AND CURRENT SENSING

(71) Applicant: COVIDIEN LP, Mansfield, MA (US)

(72) Inventors: Patrick J. Digmann, Louisville, CO (US); James A. Gilbert, Boulder, CO (US); David Farrell, Louisville, CO (US)

(73) Assignee: COVIDIEN LP, Mansfield, MA (US)

( * ) Notice: Subject to any disclaimer, the term of this patent is extended or adjusted under 35 U.S.C. 154(b) by 172 days.

(21) Appl. No.: 14/069,534

(22) Filed: Nov. 1, 2013

(65) Prior Publication Data

US 2014/0171935 A1 Jun. 19, 2014

Related U.S. Application Data

(60) Provisional application No. 61/738,060, filed on Dec. 17, 2012.

(51) Int. Cl.
*A61B 18/12* (2006.01)
*G01R 1/067* (2006.01)
(Continued)

(52) U.S. Cl.
CPC ...... *G01R 1/06772* (2013.01); *A61B 18/1206* (2013.01); *A61B 18/1402* (2013.01);
(Continued)

(58) Field of Classification Search
CPC .. A61B 2018/00648; A61B 2018/0072; A61B 2018/00767; A61B 2018/00827;
(Continued)

(56) References Cited

U.S. PATENT DOCUMENTS 4,727,874 A * 3/1988 Bowers et al. ............... 606/38
5,414,400 A 5/1995 Gris et al.
(Continued)

FOREIGN PATENT DOCUMENTS

CN 203662903 U 6/2014
DE 179607 C 3/1905
(Continued)

OTHER PUBLICATIONS

Extended European Search Report corresponding to European Application No. 13196200.3, dated Apr. 24, 2014; 6 pages.
(Continued)

*Primary Examiner* — Ronald Hupczey, Jr.
*Assistant Examiner* — Bo Ouyang

(57) ABSTRACT

An electrosurgical system is disclosed. The system includes a radio frequency output stage configured to output at least one radio frequency waveform and a current sensor coupled to the output stage and configured to output a first differentiated signal corresponding to a current of the at least one radio frequency waveform, the current sensor coupled to a first conditioning circuit configured to integrate the first differentiated signal to output a processed current signal indicative of the current. The system further includes a voltage sensor coupled to the output stage and configured to output a second differentiated signal corresponding to a voltage of the at least one radio frequency waveform, the voltage sensor coupled to a second conditioning circuit configured to integrate the second differentiated signal to output a processed voltage signal indicative of the voltage, wherein the first and second conditioning circuits have a substantially similar bandpass and phase response.

19 Claims, 11 Drawing Sheets

(51) Int. Cl.
*A61B 18/14* (2006.01)
*A61B 18/00* (2006.01)

(52) U.S. Cl.
CPC . *A61B 18/1445* (2013.01); *A61B 2018/00827* (2013.01); *A61B 2018/00892* (2013.01); *G01R 1/06788* (2013.01)

(58) Field of Classification Search
CPC ...... A61B 2018/00892; A61B 18/1233; A61B 18/10
See application file for complete search history.

(56) References Cited

U.S. PATENT DOCUMENTS

| | | | |
|---|---|---|---|
| 5,442,280 | A | 8/1995 | Baudart |
| 5,852,395 | A | 12/1998 | Bosco et al. |
| 6,094,044 | A | 7/2000 | Kustera et al. |
| 6,287,263 | B1 * | 9/2001 | Briskin .............. A61N 1/36521 600/526 |
| 6,313,623 | B1 | 11/2001 | Kojovic et al. |
| 6,624,624 | B1 | 9/2003 | Karrer et al. |
| 6,680,608 | B2 | 1/2004 | Kojovic |
| 6,731,193 | B2 | 5/2004 | Meier et al. |
| 6,791,341 | B2 | 9/2004 | Shenai et al. |
| 6,822,547 | B2 | 11/2004 | Saito et al. |
| 6,825,650 | B1 | 11/2004 | McCormack et al. |
| 7,010,438 | B2 | 3/2006 | Hancock et al. |
| 7,072,779 | B2 | 7/2006 | Hancock et al. |
| 7,106,162 | B2 | 9/2006 | Saito |
| 7,164,263 | B2 | 1/2007 | Yakymyshyn et al. |
| 7,227,441 | B2 | 6/2007 | Skendzic et al. |
| 7,227,442 | B2 | 6/2007 | Skendzic |
| 7,274,186 | B2 | 9/2007 | Yakymyshyn et al. |
| 7,279,884 | B2 | 10/2007 | Yakymyshyn et al. |
| 7,279,885 | B2 | 10/2007 | Yakymyshyn et al. |
| 7,307,410 | B2 | 12/2007 | Shiokawa et al. |
| 7,321,226 | B2 | 1/2008 | Yakymyshyn et al. |
| D574,323 | S | 8/2008 | Waaler |
| 7,474,192 | B2 | 1/2009 | Skendzic et al. |
| 7,492,162 | B2 | 2/2009 | Hachisuka et al. |
| 7,545,138 | B2 | 6/2009 | Wilkerson et al. |
| 7,564,233 | B2 | 7/2009 | Kojovic |
| 7,579,824 | B2 | 8/2009 | Rea et al. |
| 7,598,748 | B2 | 10/2009 | Hachisuka et al. |
| 7,613,578 | B2 | 11/2009 | Hagmann |
| 7,638,999 | B2 | 12/2009 | Kojovic et al. |
| 7,728,578 | B2 | 6/2010 | Etter et al. |
| 7,746,068 | B2 | 6/2010 | Mahon |
| 7,825,763 | B2 | 11/2010 | Dupraz et al. |
| 7,902,812 | B2 | 3/2011 | Kojovic |
| 7,902,813 | B2 | 3/2011 | Kojovic et al. |
| 7,959,438 | B2 | 6/2011 | Feine |
| 7,969,139 | B2 | 6/2011 | Ermisch et al. |
| 2004/0178875 | A1 | 9/2004 | Saito |
| 2004/0257061 | A1 | 12/2004 | George de Buda |
| 2007/0063664 | A1 | 3/2007 | Rhodes et al. |
| 2008/0048646 | A1 | 2/2008 | Wilkerson et al. |
| 2008/0079418 | A1 * | 4/2008 | Rea et al. ................. 324/117 R |
| 2008/0204949 | A1 * | 8/2008 | Zhou .................... H02H 1/0015 361/42 |
| 2009/0109589 | A1 * | 4/2009 | Yoo ......................... H02H 3/10 361/93.1 |
| 2009/0243590 | A1 * | 10/2009 | West et al. ................ 324/117 R |
| 2010/0283487 | A1 | 11/2010 | Juds et al. |
| 2011/0026180 | A1 | 2/2011 | Haible et al. |
| 2011/0043190 | A1 | 2/2011 | Farr |
| 2011/0050154 | A1 | 3/2011 | Farr |
| 2011/0062934 | A1 | 3/2011 | Wolf et al. |
| 2011/0089933 | A1 * | 4/2011 | Javora et al. ................. 324/127 |
| 2011/0184675 | A1 | 7/2011 | White et al. |

FOREIGN PATENT DOCUMENTS

| | | |
|---|---|---|
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 2/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1366724 A1 | 12/2003 |
| EP | 1776929 A1 | 4/2007 |
| EP | 2136216 A1 | 12/2009 |
| EP | 2281521 A1 | 2/2011 |
| EP | 2407116 A1 | 1/2012 |
| EP | 2510895 A1 | 10/2012 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| GB | 2164473 A | 3/1986 |
| JP | 63 005876 A | 1/1988 |
| JP | 2002-065690 A | 3/2002 |
| JP | 2005-185657 A | 7/2005 |
| SU | 166452 | 11/1964 |
| SU | 727201 A2 | 4/1980 |
| WO | 2000072027 A1 | 11/2000 |
| WO | 02/11634 A1 | 2/2002 |
| WO | 02/45589 A2 | 6/2002 |
| WO | 03/090635 A1 | 11/2003 |
| WO | 06/050888 A1 | 5/2006 |
| WO | 08/053532 A1 | 5/2008 |
| WO | 2010007017 A1 | 1/2010 |

OTHER PUBLICATIONS

Extended European Search Report corresponding to European Application No. 13196199.7, dated Apr. 25, 2014; 6 pages.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.

(56) References Cited

OTHER PUBLICATIONS

Prutchi et al. "Design and Development of Medical Electronic Instrumentation", John Wiley & Sons, Inc. 2005.

Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.

Muller et al. "Extended Left Hemicolectomy Using the LigaSure Vessel Sealing System", Innovations That Work; Company Newsletter; Sep. 1999.

Ogden Goertzel Alternative to the Fourier Transform: Jun. 1993 pp. 485-487, Electronics World; Reed Business Publishing, Sutton, Surrey, BG vol. 99, No. 9. 1687.

Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.

Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.

Richard Wolf Medical Instruments Corp. Brochure, "Kleppinger Bipolar Forceps & Bipolar Generator", 3 pp. Jan. 1989.

Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.

Geddes et al., "The Measurement of Physiologic Events by Electrical Impedence", Am. J. MI, Jan. Mar. 1964, pp. 16-27.

Cosman et al., "Methods of Making Nervous System Lesions", In William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Cosman et al., "Radiofrequency Lesion Generation and Its Effect on Tissue Impedance", Applied Neurophysiology 51:(1988) pp. 230-242.

Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.

Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(2005-03); pp. 160-164.

Chicharo et al. "A Sliding Goertzel Algorith" Aug. 1996, pp. 283-297, Signal Processing, Elsevier Science Publishers B.V. Amsterdam, NL vol. 52 No. 3.

Bergdahl et al., "Studies on Coagulation and the Development of an Automatic Computerized Bipolar Coagulator" Journal of Neurosurgery 75:1, (Jul. 1991) pp. 148-151.

Cosman et al., "Theoretical Aspects of Radiofrequency Lesions in the Dorsal Root Entry Zone", Neurosurgery 15: (1984) pp. 945-950.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure—Total Control at Full Speed, "The O.R. Pro 300", 1 p. Sep. 1998.

Valleylab Brochure "Valleylab Electroshield Monitoring System", 2 pp. Nov. 1995.

U.S. Appl. No. 10/406,690, filed Apr. 3, 2003, Michael S. Klicek.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 13/426,204, filed Mar. 21, 2012, Robert B. Smith.
U.S. Appl. No. 13/427,111, filed Mar. 22, 2012, Daniel A. Joseph.
U.S. Appl. No. 13/442,460, filed Apr. 9, 2012, James E. Krapohl.
U.S. Appl. No. 13/446,096, filed Apr. 13, 2012, James H. Orszulak.
U.S. Appl. No. 13/469,960, filed May 11, 2012, Robert J. Behnke, II.
U.S. Appl. No. 13/485,083, filed May 31, 2012, Robert J. Behnke, II.
U.S. Appl. No. 13/889,517, filed May 8, 2013, Behnke.
U.S. Appl. No. 13/898,632, filed May 21, 2013, Moul.
U.S. Appl. No. 13/902,011, filed May 24, 2013, Prakash.
U.S. Appl. No. 13/928,963, filed Jun. 27, 2013, Lopez.
U.S. Appl. No. 13/943,518, filed Jul. 16, 2013, Orszulak et al.
U.S. Appl. No. 13/971,553, filed Aug. 20, 2013, Behnke.
U.S. Appl. No. 13/971,596, filed Aug. 20, 2013, Collins.

European Communication dated Sep. 14, 2015, corresponding to European Patent Application No. 13196200.3; 4 pages.

Australian Examination Report from Appl. No. AU 2013273611 dated Jan. 23, 2017.

Chinese Office Action from Appl. No. CN 201310688091.8 dated Feb. 13, 2017.

Australian Examination Report issued in Appl. No. Au 2013273611 dated Aug. 1, 2017.

\* cited by examiner

SYSTEM AND METHOD FOR VOLTAGE AND CURRENT SENSING

CROSS REFERENCE TO RELATED APPLICATION

The present application claims the benefit of and priority to U.S. Provisional Application Ser. No. 61/738,060, filed on Dec. 17, 2012, the entire contents of which are incorporated herein by reference.

BACKGROUND

Technical Field

The present disclosure relates to an electrosurgical system and method for operating an electrosurgical generator. More particularly, the present disclosure relates to a system and method for measuring voltage and current in an electrosurgical generator.

Background of Related Art

Electrosurgery involves application of high radio frequency electrical current to a surgical site to cut, ablate, or coagulate tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact of body tissue with either of the separated electrodes prevents current flow.

Bipolar electrosurgery generally involves the use of forceps. A forceps is a pliers-like instrument which relies on mechanical action between its jaws to grasp, clamp and constrict vessels or tissue. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize mechanical clamping action and electrical energy to effect hemostasis on the clamped tissue. The forceps include electrosurgical conductive surfaces which apply the electrosurgical energy to the clamped tissue. By controlling the intensity, frequency and duration of the electrosurgical energy applied through the conductive plates to the tissue, the surgeon can coagulate, cauterize and/or seal tissue.

Tissue or vessel sealing is a process of liquefying the collagen, elastin and ground substances in the tissue so that they reform into a fused mass with significantly-reduced demarcation between the opposing tissue structures. Cauterization involves the use of heat to destroy tissue and coagulation is a process of desiccating tissue wherein the tissue cells are ruptured and dried.

Tissue sealing procedures involve more than simply cauterizing or coagulating tissue to create an effective seal; the procedures involve precise control of a variety of factors. For example, in order to affect a proper seal in vessels or tissue, it has been determined that two predominant mechanical parameters must be accurately controlled: the pressure applied to the tissue; and the gap distance between the electrodes (i.e., distance between opposing jaw members or opposing sealing surfaces). In addition, electrosurgical energy must be applied to the tissue under controlled conditions to ensure creation of an effective vessel seal.

Electrosurgical procedures outlined above may utilize various tissue and energy parameters in a feedback-based control system. There is continual need to improve sensors as well as systems and method for processing the sense signals.

SUMMARY

According to one aspect of the present disclosure, an electrosurgical system is disclosed. The system includes a radio frequency output stage configured to output at least one radio frequency waveform and a current sensor coupled to the output stage and configured to output a first differentiated signal corresponding to a current of the at least one radio frequency waveform, the current sensor coupled to a first conditioning circuit configured to integrate the first differentiated signal to output a processed current signal indicative of the current. The system further includes a voltage sensor coupled to the output stage and configured to output a second differentiated signal corresponding to a voltage of the at least one radio frequency waveform, the voltage sensor coupled to a second conditioning circuit configured to integrate the second differentiated signal to output a processed voltage signal indicative of the voltage, wherein the first and second conditioning circuit have a substantially similar bandpass and phase response.

According to another aspect of the disclosure, each of the first and second conditioning circuits includes a gain amplifier coupled to a single-ended amplifier coupled to a bandpass filter coupled to an integrator.

According to a further aspect of the disclosure, the radio frequency output stage includes at least one active lead and at least one return lead.

In other aspects of the present disclosure, the voltage sensor is capacitively coupled to the at least one active lead and the at least one return lead and configured to measure radio frequency voltage therebetween; and the current sensor is coupled to the at least one active lead and configured to measure radio frequency current therethrough.

According to an additional aspect of the disclosure, the current sensor includes a Rogowski coil disposed on a printed circuit board with the at least one active lead passing through the Rogowski coil.

According to a further aspect of the disclosure, the printed circuit board includes outer conductive traces coupled to the at least one active lead, the outer conductive traces interconnected by at least one via through the printed circuit board.

According to another aspect of the disclosure, the voltage sensor includes a capacitive divider comprising first and second capacitors capacively coupled to the at least one active lead and the at least one return lead; and a resistor divider comprising first and second resistors coupled to the capacitive divider.

The present disclosure also provides an electrosurgical system configured to output electrosurgical energy. The system includes a current sensor coupled to the output stage and configured to output a first differentiated signal corresponding to a current of the electrosurgical energy, the current sensor coupled to a first conditioning circuit configured to integrate the first differentiated signal to output a processed current signal indicative of the current; and a voltage sensor coupled to the output stage and configured to output a second differentiated signal corresponding to a voltage of the electro surgical energy, the current sensor coupled to a second conditioning circuit configured to integrate the second differentiated signal to output a processed voltage signal indicative of the voltage, wherein the first and second conditioning circuit have a substantially similar bandpass and phase response.

According to another aspect of the disclosure, the electrosurgical system further includes at least one active lead and at least one return lead, wherein the voltage sensor is capacitively coupled to the at least one active lead and the at least one return lead and configured to measure radio frequency voltage therebetween and the current sensor is coupled to the at least one active lead and configured to measure radio frequency current therethrough.

According to a further aspect of the disclosure, the current sensor includes a Rogowski coil disposed on a printed circuit board with the at least one active lead passing through the Rogowski coil, the printed circuit comprising outer conductive traces coupled to the at least one active lead, the outer conductive traces interconnected by at least one via through the printed circuit board.

The present disclosure further provides for a method for detecting at least one energy property of an electrosurgical generator. The method includes detecting current passing through at least one active lead of the electrosurgical generator; outputting a first differentiated signal corresponding to the current; integrating the first differentiated signal at a first conditioning circuit to output a processed current signal indicative of the current; detecting voltage between the at least one active lead and at least one return lead of the electrosurgical generator; outputting a second differentiated signal corresponding to the voltage; and integrating the second differentiated signal at a second conditioning circuit to output a processed voltage signal indicative of the voltage, wherein the first and second conditioning circuit have a substantially similar bandpass and phase response.

In other aspects of the present disclosure, the current is detected by a Rogowski coil disposed on a printed circuit board with the at least one active lead passing through the Rogowski coil, the printed circuit comprising outer conductive traces coupled to the at least one active lead, the outer conductive traces interconnected by at least one via through the printed circuit board. The Rogowski coil further includes an inner portion comprising at least one conductive trace disposed within outer coil and between the first and second dielectric intermediate layers of the printed circuit board.

In other aspects, the Rogowski coil includes an outer coil having: a plurality of top conductive traces disposed between a top dielectric layer and a first dielectric intermediate layer of the printed circuit board; a plurality of bottom conductive traces disposed between a bottom dielectric layer and a second dielectric intermediate layer of the printed circuit board, wherein the outer conductive traces are disposed over the bottom and top dielectric layers; and a plurality of inner and outer vias interconnecting the pluralities of top and bottom conductive traces. The Rogowski coil further includes an inner portion comprising at least one conductive trace disposed within outer coil and between the first and second dielectric intermediate layers of the printed circuit board.

According to another aspect of the disclosure, the voltage sensor includes: a capacitive divider comprising first and second capacitors capacively coupled to the at least one active lead and the at least one return lead; and a resistor divider comprising first and second resistors coupled to the capacitive divider.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The present disclosure provides for an electrosurgical generator having a radio frequency output stage configured to output at least one radio frequency waveform. The generator further includes a current sensor coupled to the output stage and configured to output a first differentiated signal corresponding to a current of the at least one radio frequency waveform. The current sensor is also coupled to a first conditioning circuit configured to integrate the first differentiated signal to output a processed current signal indicative of the current. The generator further includes a voltage sensor coupled to the output stage and configured to output a second differentiated signal corresponding to a voltage of the at least one radio frequency waveform. The voltage sensor is further coupled to a second conditioning circuit configured to integrate the second differentiated signal to output a processed voltage signal indicative of the voltage. The first and second conditioning circuits have a substantially similar bandpass and phase response.

A generator according to the present disclosure can perform monopolar and/or bipolar electrosurgical procedures, including vessel sealing procedures. The generator may include a plurality of outputs for interfacing with various electrosurgical instruments (e.g., a monopolar instrument, return electrode, bipolar electrosurgical forceps, footswitch, etc.). Further, the generator includes electronic circuitry configured to generate radio frequency energy specifically suited for various electrosurgical modes (e.g., cutting, blending, division, etc.) and procedures (e.g., monopolar, bipolar, vessel sealing). In embodiments, the generator may be embedded, integrated or otherwise coupled to the electrosurgical instruments providing for an all-in-one electrosurgical apparatus.

Figure 1:
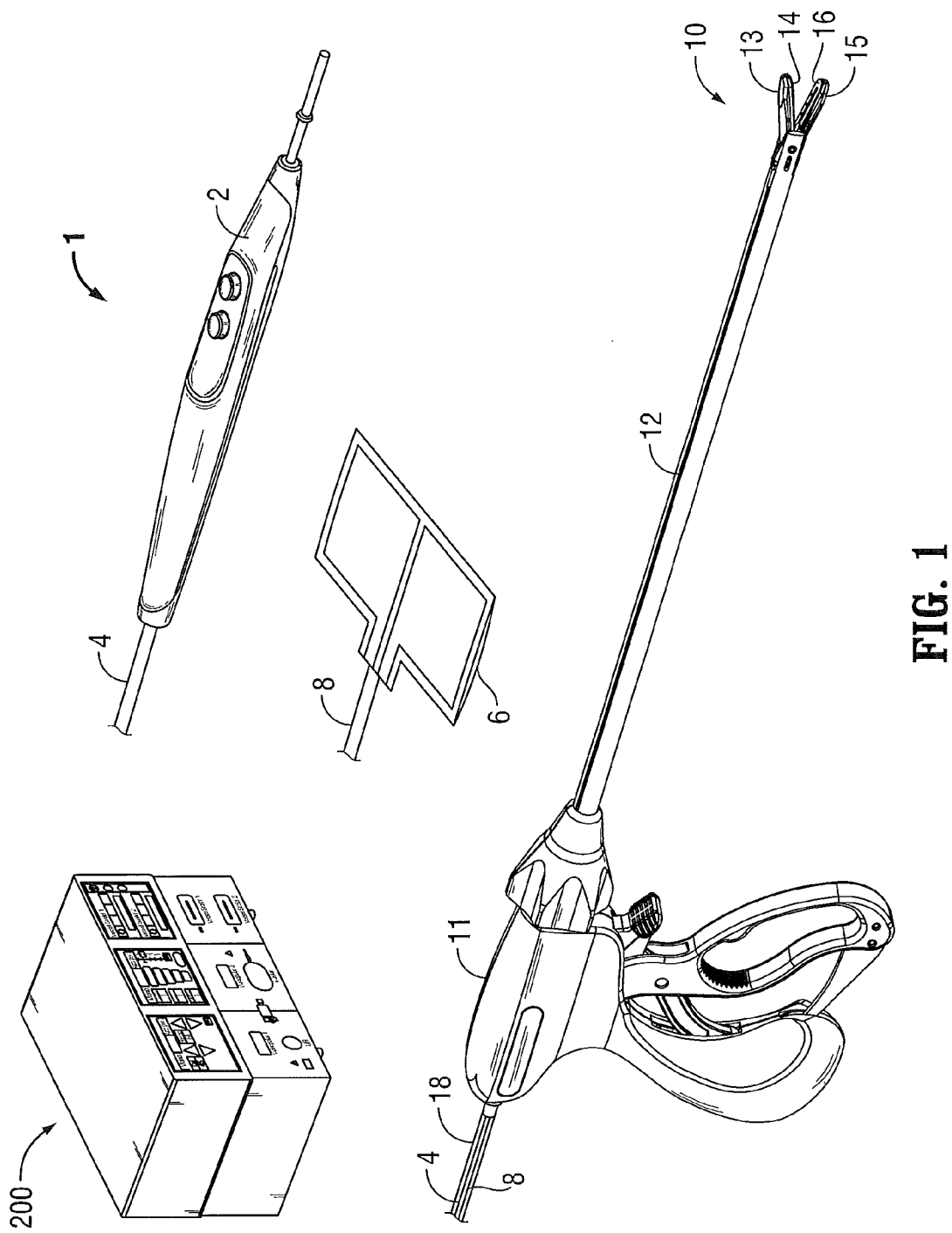
FIG. 1 is a schematic block diagram of an embodiment of an electrosurgical system according to the present disclosure.

FIG. 1 is a schematic illustration of a bipolar and monopolar electrosurgical system 1 according to the present disclosure. The system 1 may include one or more monopolar electrosurgical instruments 2 having one or more electrodes (e.g., electrosurgical cutting probe, ablation electrode(s), etc.) for treating tissue of a patient. Electrosurgical energy is supplied to the instrument 2 by a generator 200 via a supply line 4 that is connected to an active terminal 230 (FIG. 3) of the generator 200, allowing the instrument 2 to coagulate, ablate and/or otherwise treat tissue. The energy is returned to the generator 200 through a return electrode 6 via a return line 8 at a return terminal 232 (FIG. 3) of the generator 200. The system 1 may include a plurality of return electrodes 6 that are disposed on a patient to minimize the chances of tissue damage by maximizing the overall contact area with the patient. In addition, the generator 200 and the return electrode 6 may be configured for monitoring so-called "tissue-to-patient" contact to insure that sufficient contact exists therebetween to further minimize chances of tissue damage.

Figure 3:
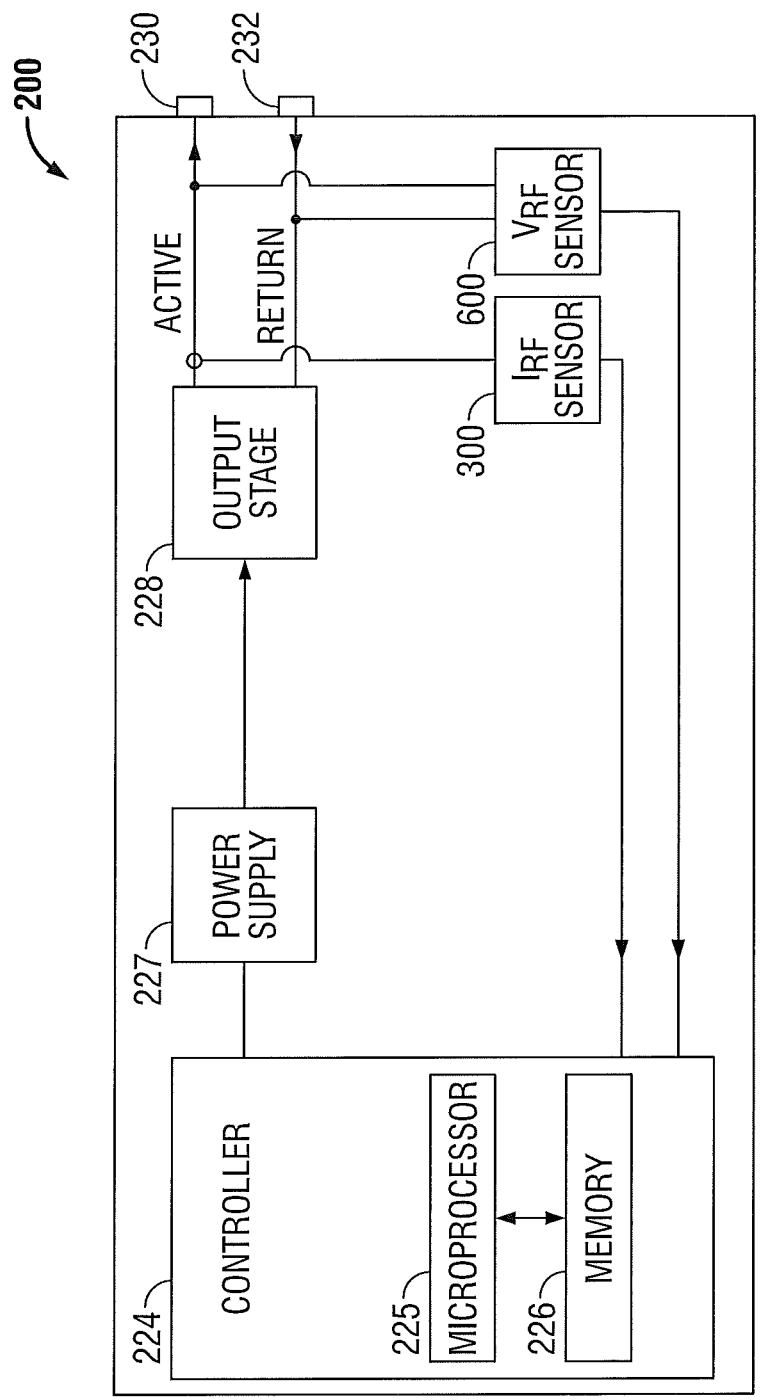
FIG. 3 is a schematic block diagram of the electrosurgical generator of FIG. 2 according to the present disclosure.

The system 1 may also include a bipolar electrosurgical forceps 10 having one or more electrodes for treating tissue of a patient. The electrosurgical forceps 10 includes a housing 11 and opposing jaw members 13 and 15 disposed at a distal end of a shaft 12. The jaw members 13 and 15 have one or more active electrodes 14 and a return electrode 16 disposed therein, respectively. The active electrode 14 and the return electrode 16 are connected to the generator 200 through cable 18 that includes the supply and return lines 4, 8 coupled to the active and return terminals 230, 232, respectively (FIG. 3). The electrosurgical forceps 10 is coupled to the generator 200 at a connector having connections to the active and return terminals 230 and 232 (e.g., pins) via a plug disposed at the end of the cable 18, wherein the plug includes contacts from the supply and return lines 4, 8 as discussed in more detail below.

Figure 2:
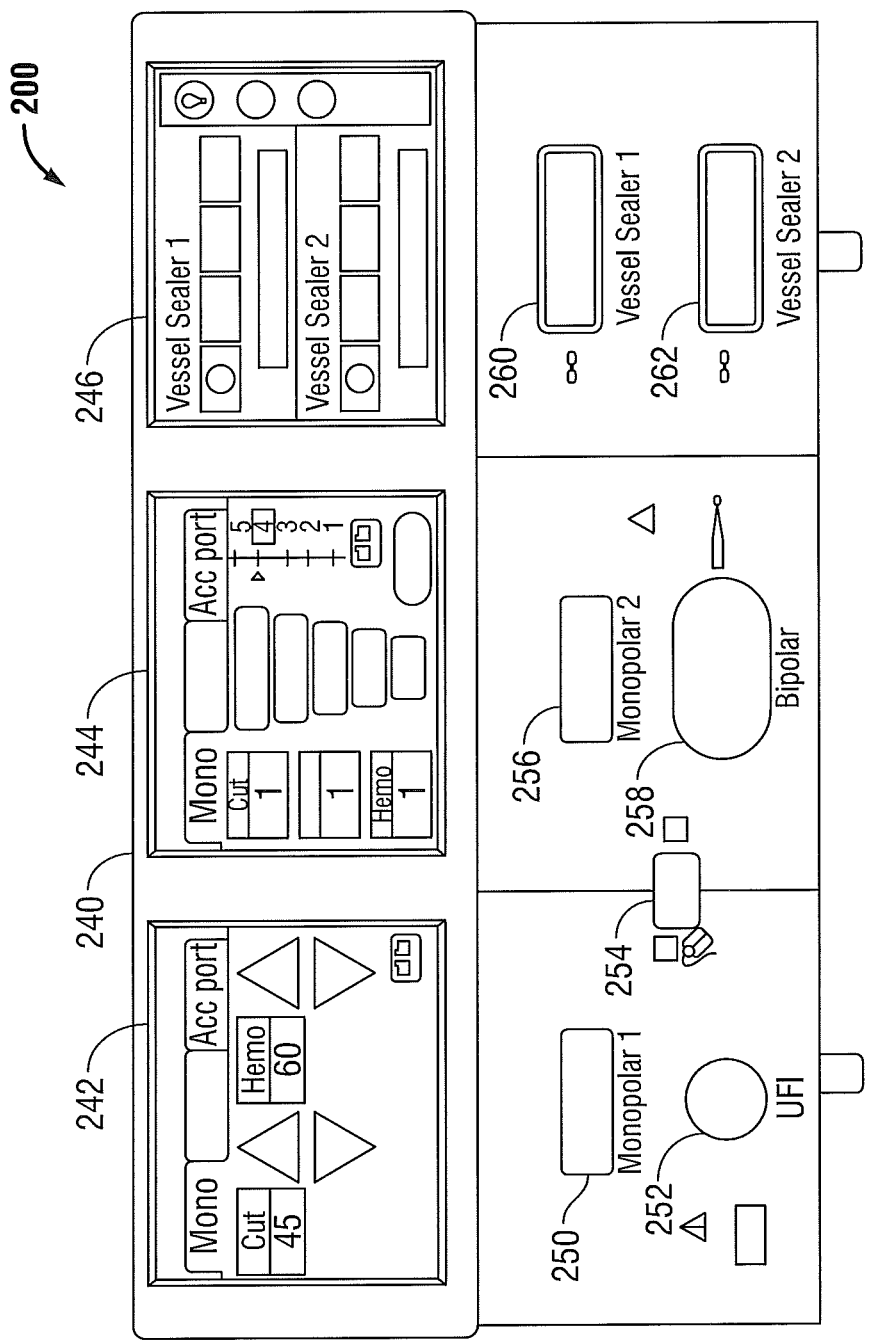
FIG. 2 is a front view of an electrosurgical generator according to the present disclosure.

With reference to FIG. 2, a front face 240 of the generator 200 is shown. The generator 200 may be any suitable type (e.g., electrosurgical, microwave, etc.) and may include a plurality of connectors 250-262 to accommodate various types of electrosurgical instruments (e.g., electrosurgical forceps 10, etc.). The connectors 250-262 may include various detection devices that can read (e.g., scan, decode, etc.) identifying information encoded or otherwise recorded on or within the plugs or cables of the instruments. The connectors 250-262 are configured to decode the information encoded on the plugs corresponding to the operating parameters of particular instruments allowing the generator 200 to preset energy delivery settings based on the connected instrument. In embodiments, data may be encoded in bar codes, electrical components (e.g., resistors, capacitors, etc.), RFID chips, magnets, non-transitory storage (e.g., non-volatile memory, EEPROM, etc.), which may then be coupled to or integrated into the plug. Corresponding detection devices may include, but are not limited to, bar code readers, electrical sensors, RFID readers, Hall Effect sensors, memory readers, etc. and any other suitable decoders configured to decode data.

The generator 200 includes one or more display screens 242, 244, 246 for providing the user with variety of output information (e.g., intensity settings, treatment complete indicators, etc.). Each of the screens 242, 244, 246 is associated with corresponding connector 250-262. The generator 200 includes suitable input controls (e.g., buttons, activators, switches, touch screen, etc.) for controlling the generator 200. The display screens 242, 244, 246 are also configured as touch screens that display a corresponding menu for the electrosurgical instruments (e.g., electrosurgical forceps 10, etc.). The user then makes inputs by simply touching corresponding menu options.

Screen 242 controls monopolar output and the devices connected to the connectors 250 and 252. Connector 250 is configured to couple to monopolar electrosurgical instrument (e.g., electrosurgical pencil) and connector 252 is configured to couple to a foot switch (not shown). The foot switch provides for additional inputs (e.g., replicating inputs of the generator 200). Screen 244 controls monopolar and bipolar output and the devices connected to the connectors 256 and 258. Connector 256 is configured to couple to other monopolar instruments. Connector 258 is configured to couple to a bipolar instrument (not shown).

Screen 246 controls bipolar sealing procedures performed by the forceps 10 that may be plugged into the connectors 260 and 262. The generator 200 outputs energy through the connectors 260 and 262 suitable for sealing tissue grasped by the forceps 10. In particular, screen 246 outputs a user interface that allows the user to input a user-defined intensity setting. The user-defined setting may be any setting that allows the user to adjust one or more energy delivery parameters, such as power, current, voltage, energy, etc. or sealing parameters, such as pressure, sealing duration, etc. The user-defined setting is transmitted to the controller 224 where the setting may be saved in memory 226. In embodiments, the intensity setting may be a number scale, such as from one to ten or one to five. In embodiments, the intensity setting may be associated with an output curve of the generator 200. The intensity settings may be specific for each forceps 10 being utilized, such that various instruments provide the user with a specific intensity scale corresponding to the forceps 10.

FIG. 3 shows a schematic block diagram of the generator 200 configured to output electrosurgical energy. The generator 200 includes a controller 224, a power supply 227, and an output stage 228. The power supply 227 may be a direct current high voltage power supply and that connects to an AC source (e.g., line voltage) and provides high voltage DC power to an output stage 228, which then converts high voltage DC power into treatment energy (e.g., ultrasonic, electrosurgical or microwave) and delivers the energy to the active terminal 230. The energy is returned thereto via the return terminal 232. The output stage 228 is configured to operate in a plurality of modes, during which the generator 200 outputs corresponding waveforms having specific duty cycles, peak voltages, crest factors, etc. In another embodiment, the generator 200 may be based on other types of suitable power supply topologies.

The controller 224 includes a microprocessor 225 operably connected to a memory 226, which may include transitory type memory (e.g., RAM) and/or non-transitory type memory (e.g., flash media, disk media, etc.). The microprocessor 225 includes an output port that is operably connected to the power supply 227 and/or output stage 228 allowing the microprocessor 225 to control the output of the generator 200 according to either open and/or closed control loop schemes. Those skilled in the art will appreciate that the microprocessor 225 may be substituted by any logic processor (e.g., control circuit) adapted to perform the calculations and/or set of instructions discussed herein.

A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then signals the power supply 227 and/or output stage 228, which then adjusts the DC and/or power supply, respectively. The controller 224 also receives input signals from the input controls of the generator 200, the instrument 2 and/or forceps 10, as described above. The controller 224 utilizes the input signals to adjust power outputted by the generator 200 in the closed control loop and/or performs other control functions thereon.

The generator 200 according to the present disclosure includes an RF current sensor 300 and an RF voltage sensor 600. The RF current sensor 300 is coupled to the active terminal 230 and provides measurements of the RF current supplied by the output stage 228. The RF voltage sensor 600 is coupled to the active and return terminals 230 and 232 provides measurements of the RF voltage supplied by the output stage 228. In embodiments, the RF current and voltage sensors 300 and 600 may be coupled to active and return leads 228a and 228b, which interconnect the active and return terminals 230 and 232 to the output stage 228, respectively. The RF current and voltage sensors 300 and 600 provide the sensed RF voltage and current signals, respectively, to the controller 224, which then may adjust output of the power supply 227 and/or the output stage 228 in response to the sensed RF voltage and current signals. Various components of the generator 200, namely, the output stage 228, the RF current and voltage sensors 300 and 600, may be disposed on a printed circuit board (PCB).

Transformers are conventionally used as current and voltage sensors as they provide a required patient isolation. However, transformers provide fluctuating readings due to temperature, signal amplitude, etc. This makes accurate readings difficult with respect to phase and gain-bandwidth of the sensor signals. As a result, the signals need to be post-processed to arrive at accurate signals. The present disclosure provides for novel RF voltage and current sensors 300 and 600 which overcome the problems of conventional sensors.

Figure 4:
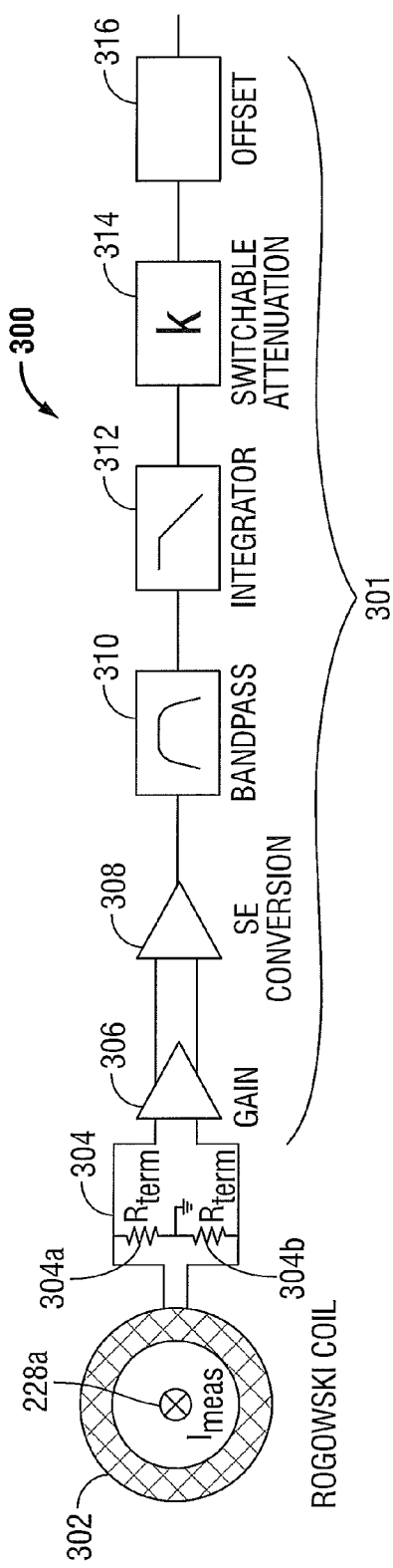
FIG. 4 is a schematic diagram of a current sensor according to the present disclosure.

FIG. 4 shows the RF current sensor 300 which includes a Rogowski coil 302. As used herein, the term "Rogowski coil" refers to an electrical device for measuring alternating current (e.g., RF current) and includes an outer conductor coil (e.g., toroid) that acts as an active conductor wrapped around an inner conductor, a so-called "Bucking coil" that acts as a return conductor with a lead carrying the current passing through the center of the coil. The coil may have any suitable shape such as helical, toroidal, etc. In embodiments, the coil may have a polygonal cross-section. The Rogowski coil may include a low permeability core (e.g., air core) and provides a voltage output having a time-derivate of the current being measured to a conditioning circuit that integrates the output to provide a voltage signal indicative of the current. In embodiments, the Rogowski coil 302 may be implemented on a printed circuit board and may include a gap so that the Rogowski coil 302 may be wrapped about the conductor carrying the current to be measured.

As described in greater detail below, the Rogowski coil 302 of the present disclosure increases common mode voltage rejection due to the connection of the Bucking coil. Further, the conditioning circuit 301 according to the present disclosure is configured as a differential amplifier that improves the common-mode rejection ratio (CMRR) unlike prior art conditioning circuits which are usually single ended and thus, fail to increase CMRR.

The Rogowski coil 302 is coupled to a conditioning circuit 301 having a resistor divider 304, which includes resistors 304a and 304b. In embodiments, the conditioning circuit 301 may be implemented as any integrator (e.g., logic processor) or differential amplifier. The resistor divider 304 removes resonance of the coil 302 at its resonant frequency. As described in further details below with respect to FIGS. 5-9, the Rogowski coil 302 is disposed about the active lead 228a, the coil 302 is configured to measure the current passing therethrough as a voltage signal. The voltage signal from the coil 302 is then supplied to an optional gain amplifier 306 which increases the amplitude of the voltage signal. The gain amplifier 306 or the coil 302, if the gain amplifier 306 is not used, is also coupled to a single-ended amplifier 308, which is in turn, coupled to a bandpass filter 310. The single ended amplifier 308 is a differential-to-single-ended converter whose function is to convert the differential signal from the coil 302 to a single-ended signal. The amplifier 308 may have a monolithic configuration that provides improved common mode rejection.

The bandpass filter 310 removes higher and lower frequency components of the voltage signal which is then transmitted to an integrator 312. Since the voltage that is induced in the Rogowski coil 302 is proportional to the rate of change of current that is flowing through the active leads 228a the integrator 312 is utilized to provide an output voltage signal that is proportional to the current.

In embodiments, the integrator 312 may be coupled to switchable attenuation circuit 314, which may include one or more actively switched components. The attenuation circuit 314 may then be coupled to additional components such as an offset circuit 316, analog-digital converters, and the like prior to supplying the signal to the controller 224.

Figure 5:
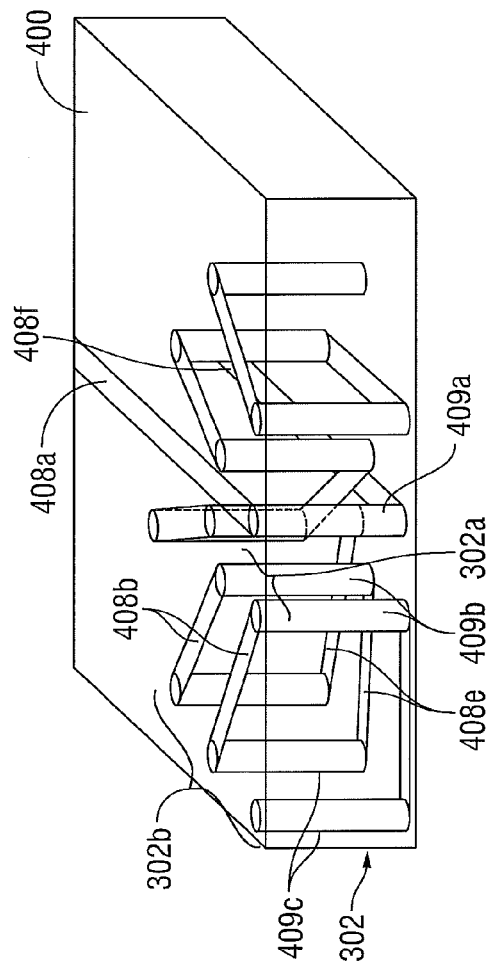
FIG. 5 is a partially-exposed, isometric view of a Rogowski coil disposed on a printed circuit board according to the present disclosure.
Figure 6:
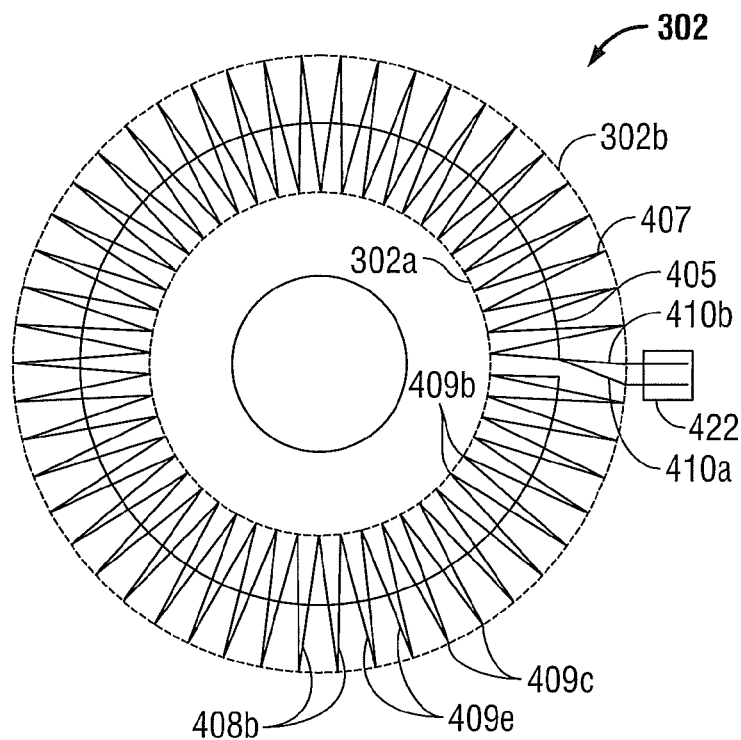
FIG. 6 is a partially-exposed, plan view of the Rogowski coil of FIG. 5 according to the present disclosure.

FIGS. 5-9 show the Rogowski coil 302 according to the present disclosure. The coil 302 has substantially a circular shape having an opening therethrough defined by inner circumferential region 302a (FIG. 6). The lead 228a is disposed through the opening 301 allowing the coil 302 to measure the current flow through the lead 228a.

As shown in FIGS. 5 and 6, the coil 302 has a substantially toroidal shape and is formed on a printed circuit board (PCB) 400 and includes and inner circumferential region 302a and an outer circumferential region 302b (FIG. 6). The coil 302 includes forming an inner portion ("Bucking coil") 405 of the coil 302 and an outer coil 407. In embodiments, the coil 302 may have any other suitable shape (e.g., having a polygonal cross-section) with the outer coil 407 wrapped about the inner portion 405 and defining an opening therethrough. In embodiments, the coil 302 may be a coil-wrapped phenolic toroid having a low permeability ($\mu_0$).

The current i(t) flowing through lead 228a produces a first magnetic field proportional to the rate of change of the sensed current i(t). The outer coil 407 detects the first magnetic field and produces a first voltage corresponding to the first magnetic field (e.g., field 1905 of FIGS. 19A-B). The outer coil 407 also detects a second magnetic field and produces a second voltage corresponding to the second magnetic field (e.g., field 1930 of FIGS. 19A-B). The second magnetic field is orthogonal to the first magnetic field and is not related to the sensed current. The inner portion 405 senses the second magnetic field and produces a third voltage proportional to the second magnetic field. The second voltage and third voltage produced have approximately the same magnitude and connected so that the cancel each other and are further removed through conditioning circuit 301.

Figure 8:
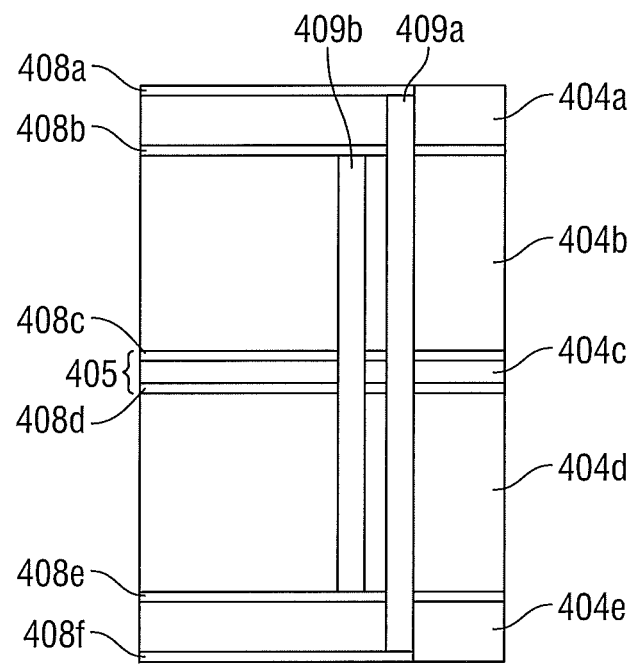
FIG. 8 is a side, cross-sectional view of the printed circuit board of FIG. 5 according to the present disclosure.
Figure 9:
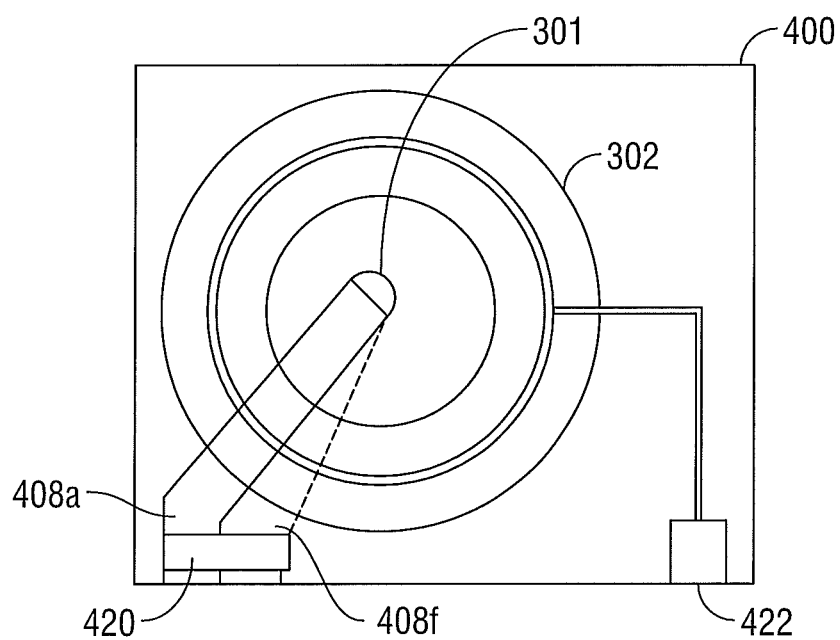
FIG. 9 is a plan view of the printed circuit board of FIG. 5 according to the present disclosure.

The PCB 400 may be a multilayer PCB formed from any suitable dielectric material, including, but not limited to composite materials composed of woven fiberglass cloth with an epoxy resin binder such as FR-4. As shown in FIG. 8, the PCB 400 includes a first or top layer 404a and a bottom layer 404e of sufficient thickness to prevent capacitive coupling between conductive traces 408b and 408e. The active lead 228a is coupled to conductive traces 408a and 408f, respectively, which are disposed over the top and bottom layers 404a and 404e as shown in FIGS. 8 and 9. The active leads 228a may be coupled to a patient side connector 420 disposed on the PCB 400 as shown in FIG. 9. The traces 408a and 408f are interconnected through the center 301 via one or more vias 409a, which pass through the entire PCB 400 (e.g., layers 404a-404e).

The outer coil 407 includes a top trace 408b disposed between the top layer 404a and an intermediate layer 404b of the PCB 400. The outer coil 407 also includes a bottom trace 408e disposed between the bottom layer 404e and an intermediate layer 404d of the PCB 400. The traces 408b and 408e are interconnected by a plurality of inner vias 409b and outer vias 409c. The layers 404a and 404e insulate the coil 302 (e.g., outer coil 407) conductive traces 408a and 408f and provide an isolation barrier between the patient and the generator 200.

Figure 7:
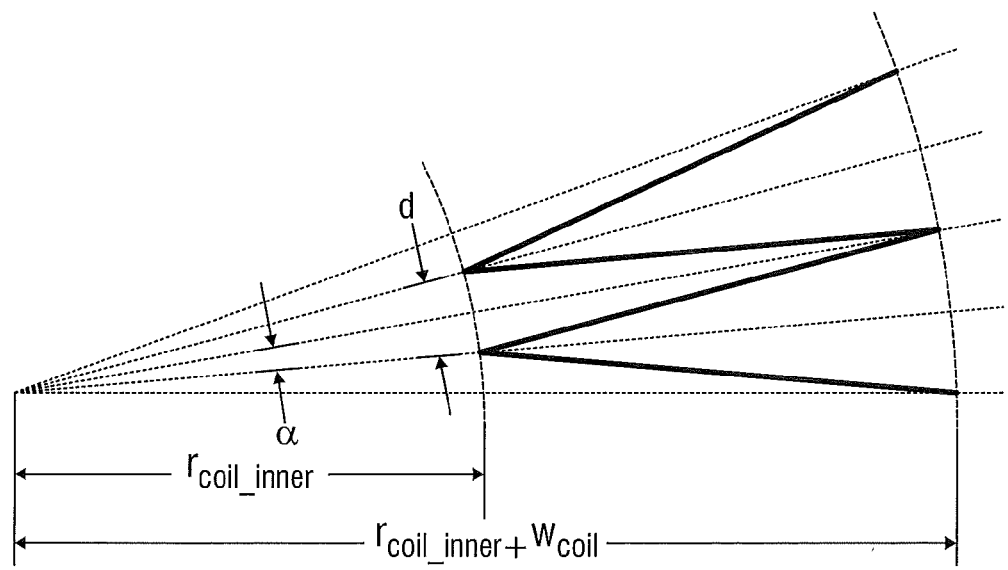
FIG. 7 is an enlarged schematic view of the Rogowski coil of FIG. 5 according to the present disclosure.
Figure 10A:
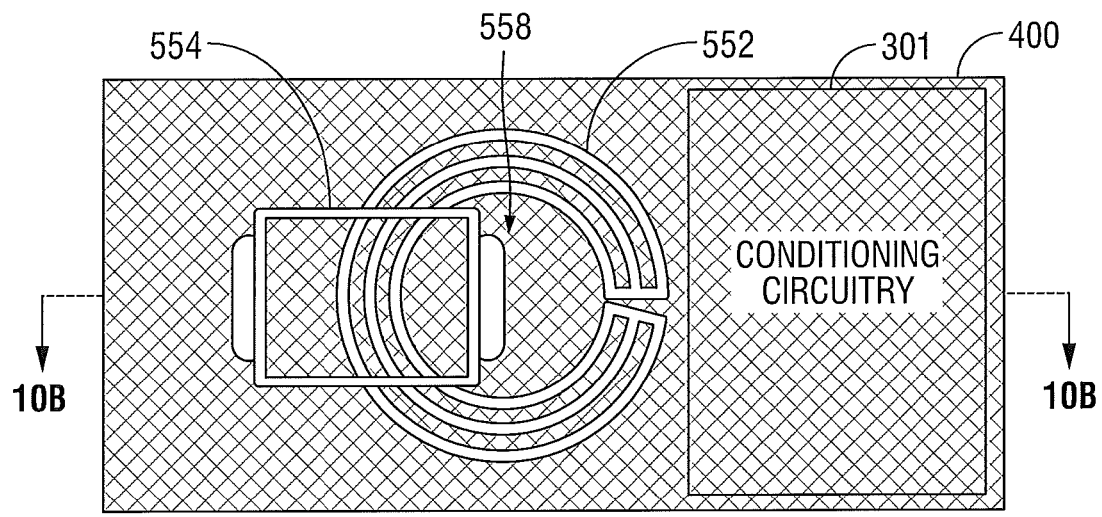
FIG. 10A is a plan view of a Rogowski coil disposed on a printed circuit board according to the present disclosure.
Figure 10B:
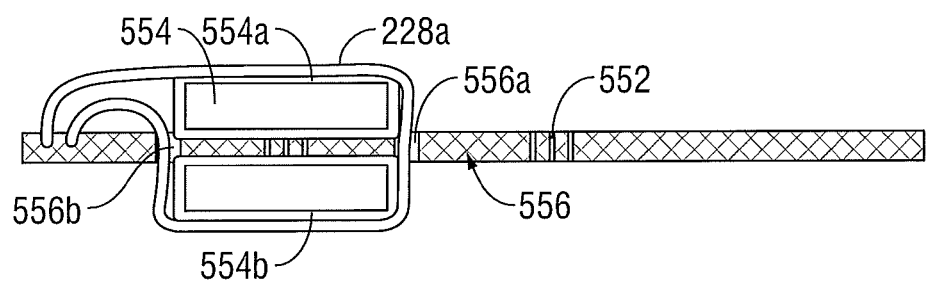
FIG. 10B is a side, cross-sectional view taken along 10B-10B of the Rogowski coil disposed on the printed circuit board according to the present disclosure.

As shown in FIGS. 5-7, the inner vias 409b are arranged to form the inner circumferential region 302a of the coil 302 and the outer vias 409c form the outer circumferential region 302b of the coil 302. The inner and outer vias 409b and 409c pass through the layers 404b, 404c, and 404d. The inner vias 409b and outer vias 409c may be disposed a concentric configuration as shown in FIGS. 10A and 10B, respectively. In a concentric configuration, corresponding inner and outer vias 409b and 409c lie along same rays. In a staggered configuration, the inner and outer vias 409b and 409c lie along alternating rays "r" as shown in FIGS. 5-7. The rays "r" are disposed at and an angle "α" relative to each other and the inner vias 409b are separated by a distance "d." Each of the inner vias 409b is connected to two neighboring outer vias 409c through traces 408a and 408e and vice versa. The interconnection of the vias 409b and 409c with the traces 408a and 408e forms a plurality of loops, which in turn, form the outer coil 407 as shown in FIG. 5.

The outer coil 407 may include any suitable number of turns, in embodiments from about 50 turns to about 100 turns. The maximum number of turns depends on the radius of the inner circumferential region 302a, via aspect ratio, thickness of the outer coil 407 and/or PCB 400, and spacing between the turns based on the limits of manufacturability of the PCB material (e.g., trace to trace, trace to via, via annular pad dimension, anything that may limit the placement of the conductors on the PCB).

With reference to FIGS. 6 and 8, the inner portion 405 is disposed within the outer coil 407 and also has a substantially circular shape. The inner portion 405 may include an upper trace 408c and a bottom trace 408d. The traces 408c and 408d are disposed over a dielectric layer 404c, such that the traces 408c and 408d are insulated from each other. The traces 408c and 408d may be electrically coupled to each other. In embodiments, the inner portion 405 may be formed from a single trace.

As shown in FIGS. 6 and 9, the coil 302 is coupled to the other components of the sensor 300 at a side connector 422, which may also disposed on the PCB 400. The coil 302 includes a first terminal 410a coupled to the inner portion 405 and a second terminal 410b coupled to the outer coil 407. In particular, the outer coil 407 is disposed over the inner portion 405 and is coupled thereto. Thus, two terminals 410a and 410b are disposed at one end of the coil 302. The interconnection between the inner portion 405 and the outer portion 407 as well as the connection to the terminals 410a and 410b may be made through the vias 409b and 409c.

The controller 224 is provided voltage signals from the sensor 300, which are then utilized to determine the current. Various formulas may be utilized by the controller 224 to determine the current. The voltage produced by the coil 302 may be calculated using the formula (I):

$$V_{OUT} = \frac{-A_{LOOP}N_{LOOPS}}{2\pi R_{COIL}} \mu_0 \frac{dI}{dt} \quad (I)$$

In formula (I), A is the area of the turn (e.g., loop) formed by the vias 409b and 409c with the traces 408a and 408b, N is the number of turns, R is the major radius of the coil 302, $\mu_0$ is the magnetic constant, dI/dt is the rate of change of the current being measured by the coil 302.

Inductance and capacitance of the coil may be calculated using the formulae (II)-(IV), respectively. Capacitance of the coil 302 is used to determine self-resonance and may be calculated using parallel-wire model formulae, namely, capacitances of inner and outer vias 409b and 409c and traces 408a and 408b.

$$L_{Coil} = \frac{\mu_0 \cdot N_{Turns}^2 \cdot t_{coil}}{2\pi} \ln\left(\frac{r_{coil\_inner} + w_{coil}}{r_{coil\_inner}}\right) \quad (II)$$

$$C_{Coil} = N_{Turns} \cdot \left(2 \cdot C_{trace-trace} + C_{via-inner} + C_{via-outer}\right) \quad (III)$$

$$C_{\parallel} = \frac{\pi \cdot \varepsilon_0 \cdot \varepsilon_r \cdot l_{trace/via}}{\ln\left(\frac{d_{between\_trace/via}}{2 \cdot r_{via/trace}} + \sqrt{\frac{d_{between\_trace/via}^2}{r_{via/trace}^2} - 1}\right)} \quad (IV)$$

In formulae (II)-(IV), in addition to the variable and constants utilized in formula (I), t is thickness (e.g., distance between conductive traces 408b and 408e), r is radius, w is the radial distance between inner and outer circumferential regions 302a and 302b, Rcoil_inner is the radial distance to the inner circumferential region 302a, l is length, $\varepsilon_0$ is vacuum permittivity constant, and $\varepsilon_r$ is the dielectric constant of the PCB.

FIGS. 10A and 10B show another embodiment of a Rogowski coil 552. The coil 552 is substantially similar to the coil 302. The coil 552 is also coupled to the conditioning circuit 301, which is disposed on the PCB 400. In this embodiment, the coil 552 is formed within the PCB 400 and the lead 228a may pass directly through the coil 552. The PCB 400 includes one or more openings 556a and 556b, with the opening 556a passing through an opening 558 defined within the coil 552. The leads 228a may be wound about a spacer 554, which is disposed between the openings 556a and 556b, which aligns the leads 228a for passage through the coil 552. The coil 552 operates in the same manner as described above with respect to the coil 302 by sensing the current passing through the leads 228a. The leads 228a may be wrapped around a spacer 554 disposed between the openings 556a and 556b, which aligns the leads 228a for passage through the coil 552. The spacer 554 may include an upper portion 554a and a lower portion 554b disposed on each side of the PCB 400.

With reference to FIGS. 4 and 11-15, conditioning circuit 301 of the sensor 300 is shown. Since the coil 302 provides a differentiating response, the output must be integrated to provide the actual response via the conditioning circuit 301 of the sensor 300. The output of the coil 302 is integrated to produce a signal that is proportional to the current in the active lead 228a. The conditioning circuit 301 provides that integration with the integrator 312. This allows for easy adjustability of the sensor gain. Gain may be set by adjusting the frequency setpoint of the integrator 312. The setpoint may be achieved by selection of hardware component values (e.g., discrete resistor or capacitor substitution), selection of software values (e.g., digital or analog potentiometers or adjustable capacitors), including programmable gain amplifiers as described in detail below, or combinations thereof.

Figure 11:
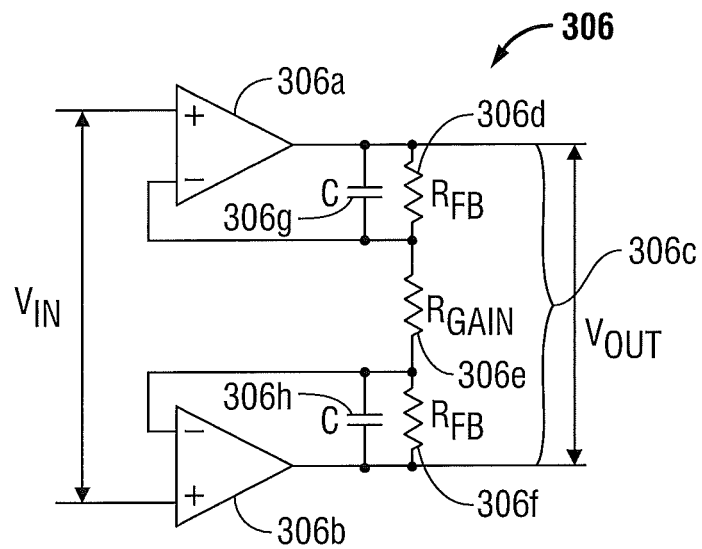
FIG. 11 is a schematic circuit diagram of a gain amplifier according to the present disclosure.

The gain amplifier 306 of the conditioning circuit 301 is shown in FIG. 11 and includes a pair of operation amplifiers 306a and 306b configured to provide differential gain without adding to the common-mode gain. The voltage signal from the coil 302 is provided to the positive terminals of the amplifiers 306a and 306b. The outputs of the amplifiers 306a are interconnected by a voltage divider network 306c including three resistors 306d, 306e, 306f. Terminal resistors 306d and 306f are coupled in parallel with capacitors 306g and 306h, respectively. The signal from the parallel circuits is coupled to the negative terminals of the amplifiers 306a and 306b, which provide closed-loop feedback thereto. These capacitors 306g and 306h provide amplifier stabilization and may also provide for the integration of the signal.

Figure 12:
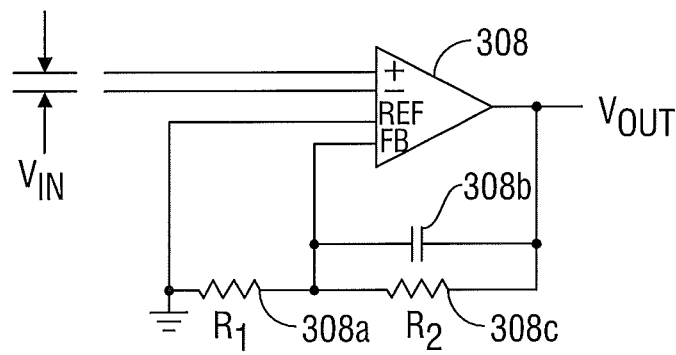
FIG. 12 is a schematic circuit diagram of a single-ended amplifier according to the present disclosure.

The output of each of the operational amplifiers 306a and 306b is provided to the single-ended amplifier 308, which is shown in FIG. 12. In particular, the output of the amplifiers 306a and 306b is supplied to the positive and negative inputs of the amplifier 308. The amplifier 308 combines the output of the amplifiers 306a and 306b to provide a single output to the bandpass filter 310. The amplifier 308 includes a closed feedback circuit having a reference signal connected to ground including a resistor 308a which is connected in parallel with a capacitor 308b and in series with a resistor 308c. The parallel circuit provides a feedback signal to a feedback input and the series circuit provides a reference signal to a reference input of the amplifier 308.

Figure 13:
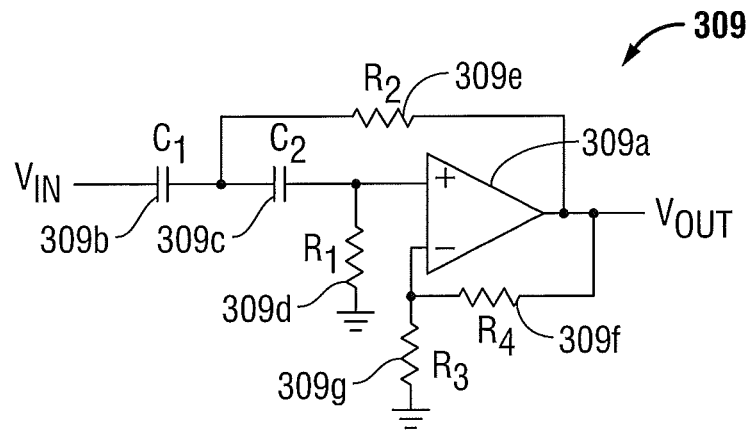
FIG. 13 is a schematic circuit diagram of a high-pass filter according to the present disclosure.
Figure 14:
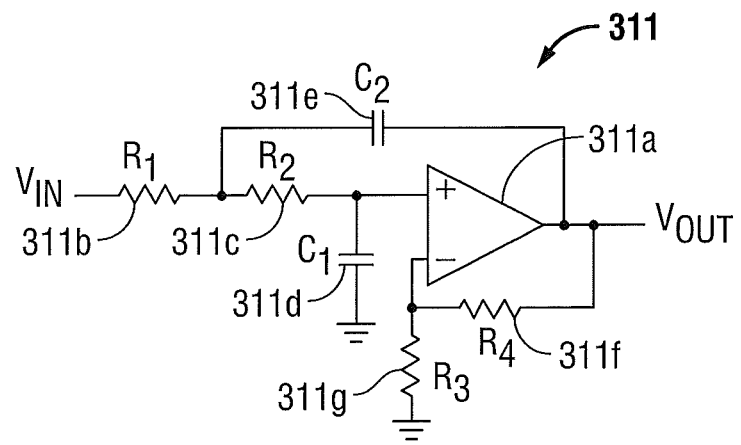
FIG. 14 is a schematic circuit diagram of a low-pass filter according to the present disclosure.
Figure 15:
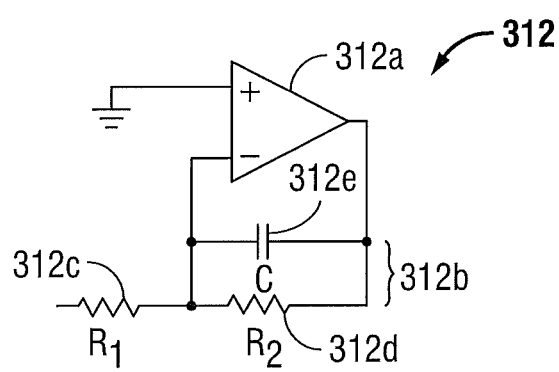
FIG. 15 is a schematic circuit diagram of an integrator according to the present disclosure.

The bandpass filter 310 includes a high-pass filter 309 and a low-pass filter 311 as shown in FIGS. 13 and 14, respectively. In embodiments, the output from the amplifier 308 may be passed through the high-pass filter 309 before being passed through the low-pass filter 311, or vice versa.

The high-pass filter 309 is configured to pass high frequencies and attenuate lower frequencies. The high-pass filter 309 includes an operational amplifier 309a. The input from the amplifier 308 or the low-pass filter 311 is provided to the positive input of the amplifier 309a having a first capacitor 309b coupled in series with a second capacitor 309c and a first resistor 309d and a second resistor 309e. The negative input of the amplifier 309a is provided by a feedback loop from a third resistor 309f coupled in series with a grounded fourth resistor 309g.

The low-pass filter 311 is configured to pass high frequencies and attenuates lower frequencies. The low-pass filter 311 includes an operational amplifier 311a. The input from the amplifier 308 or the high-pass filter 309 is provided to the positive input of the amplifier 311a having a first resistor 311b coupled in series with a second resistor 311c and a first capacitor 311d and a second capacitor 311e. The negative input of the amplifier 311a is provided by a feedback loop from a third resistor 311f coupled in series with a grounded fourth resistor 311g.

Since the voltage that is induced in the Rogowski coil 302 is proportional to the rate of change of current that is flowing through the active leads 228a the integrator 312 is utilized to provide an output voltage signal that is proportional to the current. In embodiments, a leaky integrator may be used. As used herein the term "leaky integrator" refers to an integrator having a low-pass filter as described in further detail below with respect to FIG. 14. The integrator 312 includes an amplifier 312a with a positive input thereof coupled to a ground. The input from the bandpass filter 310 is fed through a low-pass filter 312b, which includes a first resistor 312c coupled in series with a second resistor 312d that is coupled in parallel with a capacitor 312e. The second resistor 312d and the capacitor 312e are also coupled to the output of the amplifier 312a thereby providing a closed loop feedback thereto. The input signal is then fed to the negative input of the amplifier 312a. The filter 312b may be used in lieu of or in combination with the bandpass filter 310.

The integrator 312 provides a negative slope of voltage gain verses frequency. This compensates, or flattens the opposite slope of the signal coming from the coil 302. Further, the integrator 312 has extremely high DC gain. The frequency band of interest for the generator 200 is well above DC. The integrator gain would create problems if a DC offset were present at its input. The high-pass portion of the band-pass filter 310 reduces the low frequency components and reduces any DC offset, which mitigates issues caused by the integrator's amplification of these components.

Figure 16:
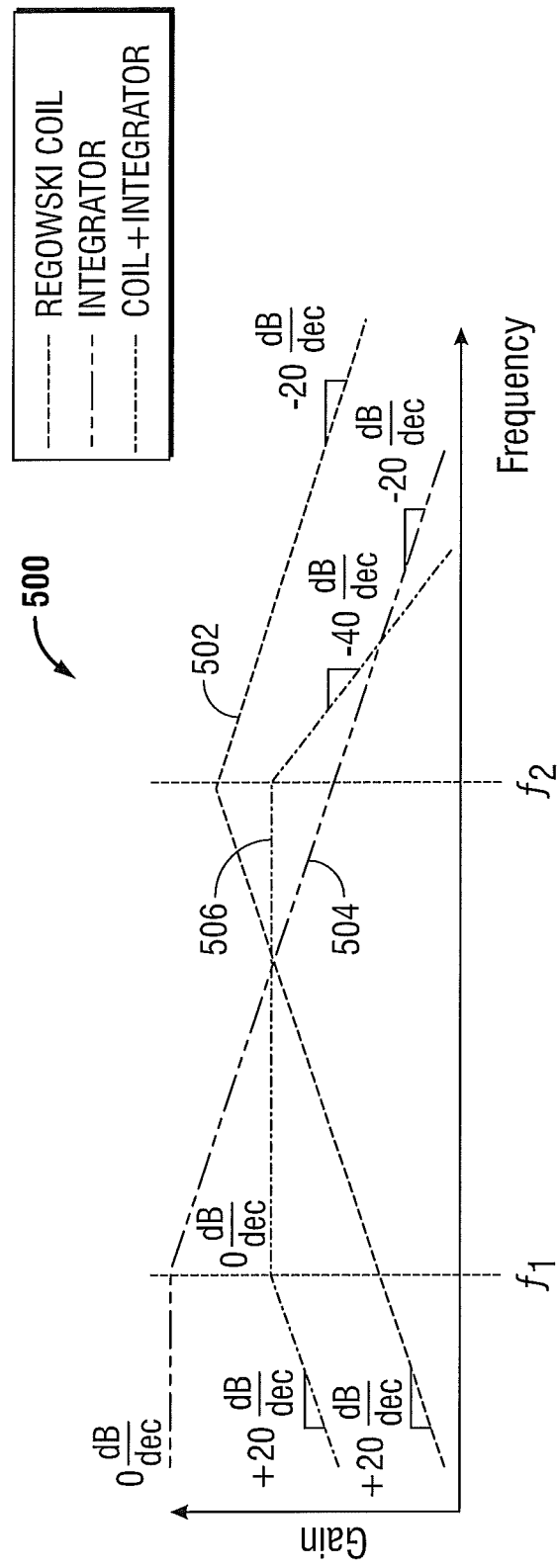
FIG. 16 is a plot of a bandwidth of the current sensor according to the present disclosure.

FIG. 16 shows a graph 500 illustrating individual gain response of the coil 302, the integrator 312, and the combined response of the coil 302 and the integrator 312. The graph 500 shows the overall response of the coil 302 as a plot 502, the response of the integrator 312 as a plot 504, and the combined response of the coil 302 and the integrator 312 of the sensor 300 as a plot 506, which is a combination of the plots 502 and 504. Frequency, f1, is determined by the response of the integrator 312 and frequency, f2, is determined by the resonant frequency of the coil 302.

Figure 17:
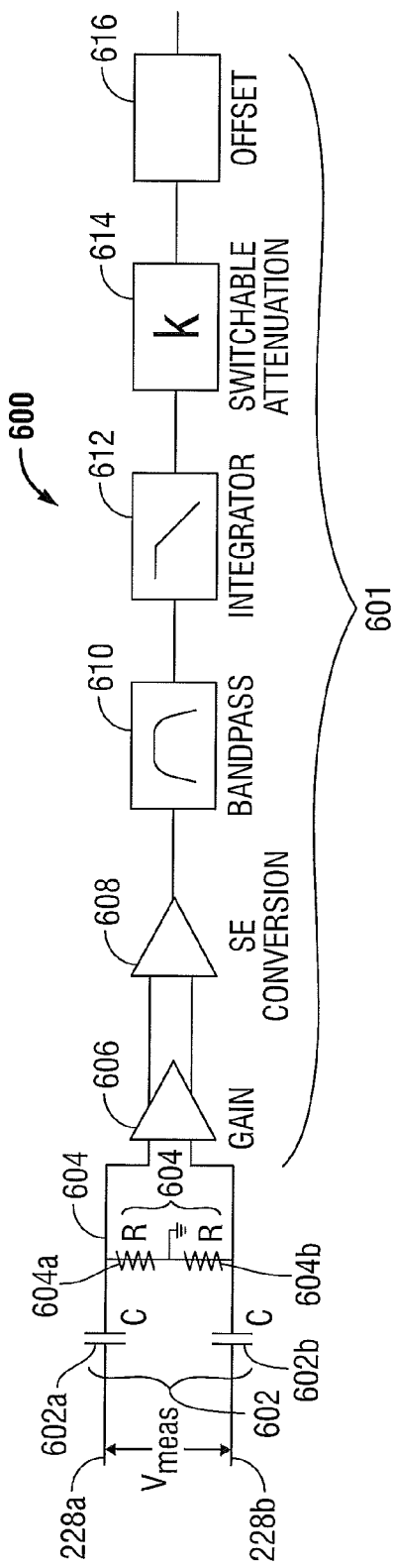
FIG. 17 is a schematic diagram of a voltage sensor according to the present disclosure.

FIG. 17 shows the RF voltage sensor 600. The sensor 600 is configured as a capacitive divider 602 including first and second capacitors 602a and 602b coupled to conditioning circuit 601. The conditioning circuit 601 of the sensor 600 is substantially similar to the conditioning circuit of the sensor 300 and includes the same components, which are designated using like numerals. The capacitive divider 602 is coupled to a resistor divider 604 including first and second resistors 604a and 604b. The voltage is then supplied to an optional gain amplifier 606 which increases the amplitude of the voltage signal. The gain amplifier 606 or the capacitive divider 602, if the gain amplifier 606 is not used, is coupled to a single-ended amplifier 608, which is in turn, coupled to a bandpass filter 610. The single ended amplifier 608 is a differential-to-single-ended converter whose function is to convert the differential signal from the coil 602 to a single-ended signal. The amplifier 608 may have a monolithic configuration that provides improved common mode rejection.

The bandpass filter 610 removes higher and lower frequency components of the voltage signal which is then transmitted to an integrator 612. Since the voltage that is induced in the capacitive divider 602 is proportional to the rate of change of current that is flowing through the active and return leads 228a and 228b the integrator 612 is utilized to provide an output voltage signal that is proportional to the sensed RF voltage.

In embodiments, the integrator 612 may be coupled to switchable attenuation circuit 614, which may include one or more actively switched components. The attenuation circuit 614 may then be coupled to additional components such as an offset circuit 616, analog-digital converters, and the like prior to supplying the signal to the controller 224.

Figure 18:
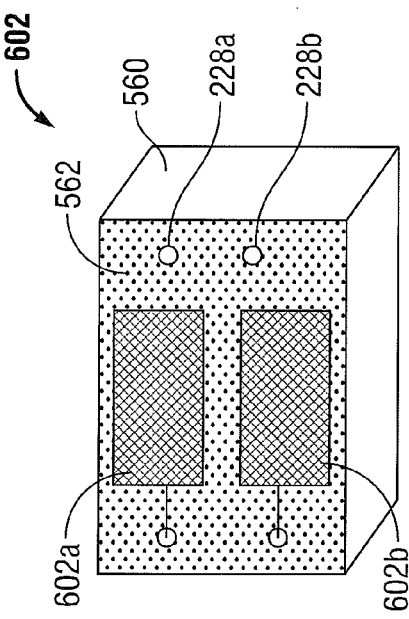
FIG. 18 is a plan, cross-sectional view of the voltage sensor according to the present disclosure.

The capacitive divider 602 is shown in more detail in FIG. 18. The capacitors 602a and 602b are a matched pair of capacitors having substantially similar dielectric properties. The capacitors 602a and 602b may be plate capacitors that are disposed in a housing 560 are secured therein via a potting material 562. Potting material 562 may be any suitable dielectric material that is injection molded or otherwise provided into the housing 560. The material 562 also provides additional insulation between the capacitors 602a and 602b. The capacitive divider 602 may be disposed in proximity to the active and return leads 228a and 228b allowing the capacitors to measure the voltage therebetween.

The capacitors 602a and 602b are insulated from the active and return leads 228a and 228b and provide an isolation barrier between the patient and the generator 200. The capacitors 602a and 602b are disposed in proximity to the active and return leads 228a and 228b, such that the voltage is capacitively detected by the capacitors 602a and 602b. In other words, the capacitors 602a and 602b are capacitively coupled to the active and return leads 228a and 228b. The capacitors 602a and 602b may be plate capacitors, each having one place connected to the active and return leads 228a and 228b and the other plate connected to the conditioning circuit 601. In embodiments, the plates of the capacitors 602a and 602b may be disposed on opposing sides of a PCB. Thus, the material (e.g., PCB) between the plates provides the insulation. As used herein the term "capacitively coupled" denotes indirect electrical contact between the capacitors 602a and 602b and the active and return leads 228a and 228b, such that electrical current passing through the return leads 228a and 228b is detected through a dielectric.

The capacitor 602a and the resistor 604a as well as the capacitor 602b and the resistor 604b combinations create similar voltage response as the coil 302. Thus, matching the gain amplifier 606, the single-ended amplifier 608, the bandpass filter 610, and the integrator 612 to the gain amplifier 306, the single-ended amplifier 308, the bandpass filter 310, and the integrator 312 allows for matching the bandpass (e.g., gain) and phase response of the sensors 300 and 600. In embodiments, the conditioning circuits 300 and 600 may have a substantially similar bandpass and phase response. As used herein, the term "substantially similar" denotes a difference between the bandpass and phase response of the conditioning circuits 300 and 600 of no more than from about 1 degree difference between voltage and current channels to about 15 degrees, in embodiments, from about 2 degrees to about 10 degrees, in further embodiments about 5 degrees. Since the integration of both current and voltage sensors 300 and 600 may be performed by identical conditioning circuit 301 and 601, the two signals are matched in gain and phase characteristics, which provides for accurate and precise representation of real power dissipated by the tissue during electrosurgery.

The capacitors 602a and 602b block the RF voltage delivered to the patient and provide a low sense voltage across the resistors 604a and 604b. The differential gain of the conditioning capacitors 602a and 602b is substantially equal to the common-mode gain due to close matching of the capacitor 602a and the resistor 604a as well as the capacitor 602b and the resistor 604b combinations. Thus, the common-mode rejection ratio effectively is the common-mode rejection ratio of the conditioning circuit 601. As a result, if the capacitors 602a and 602b and/or the resistors 604a and 604b are not matched closely, the common mode signal become a differential mode signal thereby generating an error signal.

The voltage and current sensors of the present disclosure provide various improvements over transformers in terms of isolation. In the Rogowski coil implementation the isolation and dielectric strength come from adequate wire insulation or adequate PCB material insulation. As these are inherent in the design and do not need to be applied manually as in a transformer implementation. This reduces the manufacturing costs.

Similarly, the matching of the capacitors can be accomplished via the construction techniques of the PCB manufacture. This ensures very closely matched parts. In addition to excellent matching characteristics the dielectric strength is provided by the PCB manufacture. The capacitance is controlled very precisely in this instance and is much lower than in the transformer implementation. These aspects are important for patient safety and improved operation of the sensors.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system, comprising:
 a radio frequency output stage configured to output a radio frequency waveform having a current and a voltage;
 a current sensor including a Rogowski coil coupled to the output stage and configured to output a first differentiated signal corresponding to the current of the radio frequency waveform;
 a first conditioning circuit including:
  a first resistor divider;
  a first single-ended amplifier configured to convert the first differentiated signal to a first single-ended signal;

a first bandpass filter; and
a first integrator coupled to the Rogowski coil and configured to integrate the first single-ended signal to output a processed current signal proportional to the current;
a voltage sensor including a capacitive divider coupled to the output stage and configured to output a second differentiated signal corresponding to the voltage of the radio frequency waveform;
a second conditioning circuit including:
a second resistor divider;
a second single-ended amplifier configured to convert the second differentiated signal to a second single-ended single;
a second bandpass filter; and
a second integrator coupled to the capacitive divider and configured to integrate the second single-ended signal to output a processed voltage signal proportional to the voltage,
wherein the first and second conditioning circuits have a matched gain and phase response; and
a controller coupled to the first and second conditioning circuits and configured to adjust the radio frequency waveform output by the output stage based on at least one of the processed current signal or the processed voltage signal.

2. The electrosurgical system according to claim 1, wherein the radio frequency output stage includes an active lead and a return lead.

3. The electrosurgical system according to claim 2, wherein the voltage sensor is capacitively coupled to the active lead and the return lead and configured to measure radio frequency voltage therebetween, and the current sensor is coupled to the active lead and configured to measure radio frequency current therethrough.

4. The electrosurgical system according to claim 3, wherein the Rogowski coil is disposed on a printed circuit board with the active lead passing through the Rogowski coil.

5. The electrosurgical system according to claim 4, wherein the printed circuit board includes outer conductive traces coupled to the active lead, the outer conductive traces interconnected by a via through the printed circuit board.

6. The electrosurgical system according to claim 5, wherein the Rogowski coil includes:
an outer coil including:
a plurality of top conductive traces disposed between a top dielectric layer and a first dielectric intermediate layer of the printed circuit board;
a plurality of bottom conductive traces disposed between a bottom dielectric layer and a second dielectric intermediate layer of the printed circuit board, wherein the outer conductive traces are disposed over the bottom and top dielectric layers; and
a plurality of inner and outer vias interconnecting the pluralities of top and bottom conductive traces; and
an inner portion including a conductive trace disposed within the outer coil and between the first and second dielectric intermediate layers of the printed circuit board.

7. The electrosurgical system according to claim 3, wherein the capacitive divider includes first and second capacitors capacitively coupled to the active lead and the return lead, the voltage sensor further including a resistor divider including first and second resistors coupled to the capacitive divider.

8. An electrosurgical system configured to output electrosurgical energy, comprising:
a current sensor including a Rogowski coil coupled to an output stage and configured to output a first differentiated signal corresponding to a current of the electrosurgical energy;
a first conditioning circuit including:
a first resistor divider;
a first single-ended amplifier configured to convert the first differentiated signal to a first single-ended signal;
a first bandpass filter; and
a first integrator coupled to the Rogowski coil and configured to integrate the first single-ended signal to output a processed current signal proportional to the current;
a voltage sensor including a capacitive divider coupled to the output stage and configured to output a second differentiated signal corresponding to a voltage of the electrosurgical energy;
a second conditioning circuit including:
a second resistor divider;
a second single-ended amplifier configured to convert the second differentiated signal to a second single-ended single;
a second bandpass filter; and
a second integrator coupled to the capacitive divider and configured to integrate the second single-ended signal to output a processed voltage signal proportional to the voltage,
wherein the first and second conditioning circuits have a matched gain and phase response; and
a controller coupled to the first and second conditioning circuits and configured to adjust the electrosurgical energy output by the output stage based on at least one of the processed current signal or the processed voltage signal.

9. The electrosurgical system according to claim 8, further including an active lead and a return lead, wherein the voltage sensor is capacitively coupled to the active lead and the return lead and configured to measure radio frequency voltage therebetween, and the current sensor is coupled to the active lead and configured to measure radio frequency current therethrough.

10. The electrosurgical system according to claim 9, wherein the Rogowski coil is disposed on a printed circuit board with the active lead passing through the Rogowski coil, the printed circuit including outer conductive traces coupled to the active lead, the outer conductive traces interconnected by a via through the printed circuit board.

11. The electrosurgical system according to claim 10, wherein the Rogowski coil includes:
an outer coil including:
a plurality of top conductive traces disposed between a top dielectric layer and a first dielectric intermediate layer of the printed circuit board;
a plurality of bottom conductive traces disposed between a bottom dielectric layer and a second dielectric intermediate layer of the printed circuit board, wherein the outer conductive traces are disposed over the bottom and top dielectric layers; and
a plurality of inner and outer vias interconnecting the pluralities of top and bottom conductive traces; and
an inner portion including a conductive trace disposed within the outer coil and between the first and second dielectric intermediate layers of the printed circuit board.

12. The electrosurgical system according to claim 9, wherein the capacitive divider includes first and second capacitors capacitively coupled to the active lead and the return lead, the voltage sensor further including a resistor divider including first and second resistors coupled to the capacitive divider.

13. A method for detecting an energy property of an electrosurgical generator, comprising:
   detecting current passing through an active lead of an electrosurgical generator;
   outputting a first differentiated signal corresponding to the current;
   converting the first differentiated signal to a first single-ended signal at a first single-ended amplifier of a first conditioning circuit;
   integrating the first single-ended signal at a first integrator of the first conditioning circuit to output a processed current signal proportional to the current;
   delivering the processed current signal indicative of the current to a controller for adjusting electrosurgical energy output by the electrosurgical generator;
   detecting voltage between the active lead and a return lead of the electrosurgical generator;
   outputting a second differentiated signal corresponding to the voltage;
   converting the second differentiated signal to a second single-ended single at a single-ended amplifier of a second conditioning circuit;
   integrating the second single-ended signal at a second integrator of a second conditioning circuit to output a processed voltage signal proportional to the voltage,
   wherein the first and second conditioning circuits have a matched gain and phase response; and
   delivering the processed voltage signal indicative of the voltage to the controller for adjusting electrosurgical energy output by the electrosurgical generator.

14. The method according to claim 13, wherein the current is detected by a Rogowski coil disposed on a printed circuit board with the active lead passing through the Rogowski coil, the printed circuit including outer conductive traces coupled to the active lead, the outer conductive traces interconnected by a via through the printed circuit board.

15. The method according to claim 14, wherein the Rogowski coil includes:
   an outer coil including:
      a plurality of top conductive traces disposed between a top dielectric layer and a first dielectric intermediate layer of the printed circuit board;
      a plurality of bottom conductive traces disposed between a bottom dielectric layer and a second dielectric intermediate layer of the printed circuit board, wherein the outer conductive traces are disposed over the bottom and top dielectric layers; and
      a plurality of inner and outer vias interconnecting the pluralities of top and bottom conductive traces.

16. The method according to claim 15, wherein the Rogowski coil further includes an inner portion including a conductive trace disposed within the outer coil and between the first and second dielectric intermediate layers of the printed circuit board.

17. The method according to claim 13, wherein the current is detected by a voltage sensor including:
   the second conditioning circuit;
   a capacitive divider coupled to the second integrator of the second conditioning circuit and including first and second capacitors capacitively coupled to the active lead and the return lead; and
   a resistor divider including first and second resistors coupled to the capacitive divider.

18. The electrosurgical system according to claim 1, wherein the processed current signal indicative of the current of the radio frequency waveform output by the output stage is supplied to the controller through a first input, and the processed voltage signal indicative of the voltage of the radio frequency waveform output by the output stage is supplied to the controller through a second input, separate from the first input.

19. The electrosurgical system according to claim 8, wherein the processed current signal indicative of the current of the electrosurgical energy output by the output stage is supplied to the controller through a first input, and the processed voltage signal indicative of the voltage of the electrosurgical energy output by the output stage is supplied to the controller through a second input, separate from the first input.

* * * * *

UNITED STATES PATENT AND TRADEMARK OFFICE
CERTIFICATE OF CORRECTION

| | | |
|---|---|---|
| PATENT NO. | : 9,921,243 B2 | Page 1 of 1 |
| APPLICATION NO. | : 14/069534 | |
| DATED | : March 20, 2018 | |
| INVENTOR(S) | : Digmann et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 303 days.

Signed and Sealed this

Twenty-fifth Day of September, 2018

Andrei Iancu
*Director of the United States Patent and Trademark Office*